(12) United States Patent
Uppaluri et al.

(10) Patent No.: US 7,796,795 B2
(45) Date of Patent: *Sep. 14, 2010

(54) SYSTEM AND METHOD FOR COMPUTER AIDED DETECTION AND DIAGNOSIS FROM MULTIPLE ENERGY IMAGES

(75) Inventors: Renuka Uppaluri, Pewaukee, WI (US); Gopal Biligeri Avinash, Menomonee Falls, WI (US); Carson Hale Thomas, Brookfield, WI (US); John Michael Sabol, Sussex, WI (US); Kadri Nizar Jabri, Waukesha, WI (US); Amber Elaine Rader, Mansfield, OH (US)

(73) Assignee: General Electric Co., Schenectady, NY (US)

( * ) Notice: Subject to any disclaimer, the term of this patent is extended or adjusted under 35 U.S.C. 154(b) by 106 days.

This patent is subject to a terminal disclaimer.

(21) Appl. No.: 11/859,035

(22) Filed: Sep. 21, 2007

(65) Prior Publication Data

US 2008/0031507 A1 Feb. 7, 2008

Related U.S. Application Data

(63) Continuation of application No. 10/065,854, filed on Nov. 26, 2002, now Pat. No. 7,295,691.

(51) Int. Cl.
*G06K 9/00* (2006.01)
(52) U.S. Cl. .................. 382/128; 382/130; 382/131
(58) Field of Classification Search .......... 382/128–134
See application file for complete search history.

(56) References Cited

U.S. PATENT DOCUMENTS

| 4,571,491 | A | 2/1986 | Vinegar et al. |
| 4,626,688 | A | 12/1986 | Barnes |
| 4,788,429 | A | 11/1988 | Wilson |
| 4,789,930 | A | 12/1988 | Sones et al. |
| 4,792,900 | A | 12/1988 | Sones et al. |
| 4,837,686 | A | 6/1989 | Sones et al. |
| 4,907,156 | A | 3/1990 | Doi et al. |
| 4,963,746 | A | 10/1990 | Morgan et al. |
| 4,975,933 | A | 12/1990 | Hampel |
| 4,980,904 | A | 12/1990 | Sones et al. |

(Continued)

FOREIGN PATENT DOCUMENTS

EP        0682497        5/1994

(Continued)

OTHER PUBLICATIONS

FR Patent Application No. 0305690, Search Report, Apr. 6, 2010.

*Primary Examiner*—Wes Tucker

(57) ABSTRACT

A method, system, and storage medium for computer aided processing of an image set includes employing a data source, the data source including an image set acquired from X-ray projection imaging, x-ray computed tomography, or x-ray tomosynthesis, defining a region of interest within one or more images from the image set, extracting feature measures from the region of interest, and reporting at least one of the feature measures on the region of interest. The method may be employed for identifying bone fractures, disease, obstruction, or any other medical condition.

20 Claims, 16 Drawing Sheets

U.S. PATENT DOCUMENTS

| | | | |
|---|---|---|---|
| 5,068,788 A | 11/1991 | Goodenough et al. |
| 5,115,394 A | 5/1992 | Walters |
| 5,123,037 A | 6/1992 | Picard |
| 5,155,365 A | 10/1992 | Cann et al. |
| 5,235,628 A | 8/1993 | Kalender |
| 5,247,559 A | 9/1993 | Ohtsuchi et al. |
| RE34,511 E | 1/1994 | O'Neill et al. |
| 5,289,374 A | 2/1994 | Doi et al. |
| 5,319,549 A | 6/1994 | Katsuragawa et al. |
| 5,335,260 A | 8/1994 | Arnold |
| 5,376,795 A | 12/1994 | Hasegawa et al. |
| 5,402,338 A | 3/1995 | Ito |
| 5,430,787 A | 7/1995 | Norton |
| 5,442,672 A | 8/1995 | Bjorkholm et al. |
| 5,463,548 A | 10/1995 | Asada et al. |
| 5,490,196 A | 2/1996 | Rudich et al. |
| 5,557,687 A | 9/1996 | Hara |
| 5,622,171 A | 4/1997 | Asada et al. |
| 5,648,997 A | 7/1997 | Chao |
| 5,665,971 A | 9/1997 | Chen et al. |
| 5,732,697 A | 3/1998 | Zhang et al. |
| 5,748,705 A | 5/1998 | Stein et al. |
| 5,762,608 A | 6/1998 | Warne et al. |
| 5,764,721 A | 6/1998 | Light et al. |
| 5,769,074 A | 6/1998 | Barnhill et al. |
| 5,771,269 A | 6/1998 | Chao |
| 5,838,758 A | 11/1998 | Krug et al. |
| 5,850,465 A | 12/1998 | Shimura et al. |
| 5,873,824 A | 2/1999 | Doi et al. |
| 5,900,170 A | 5/1999 | Marcin, Jr. et al. |
| 5,910,972 A | 6/1999 | Ohkubo et al. |
| 5,914,059 A | 6/1999 | Marcin, Jr. et al. |
| 5,930,327 A | 7/1999 | Lin |
| 5,931,780 A | 8/1999 | Giger et al. |
| 6,008,208 A | 12/1999 | Petrie et al. |
| 6,018,562 A | 1/2000 | Willson |
| 6,052,433 A | 4/2000 | Chao |
| 6,058,322 A | 5/2000 | Nishikawa et al. |
| 6,088,423 A | 7/2000 | Krug et al. |
| 6,088,473 A | 7/2000 | Xu et al. |
| 6,103,402 A | 8/2000 | Marcin, Jr. et al. |
| 6,132,724 A | 10/2000 | Blum |
| 6,141,437 A | 10/2000 | Xu et al. |
| 6,173,034 B1 | 1/2001 | Chao |
| 6,185,272 B1 | 2/2001 | Hiraoglu et al. |
| 6,205,348 B1 | 3/2001 | Giger et al. |
| 6,207,958 B1 | 3/2001 | Giakos |
| 6,240,201 B1 | 5/2001 | Xu et al. |
| 6,248,063 B1 | 6/2001 | Barnhill et al. |
| 6,306,087 B1 | 10/2001 | Barnhill et al. |
| RE37,536 E | 2/2002 | Barnes |
| 6,370,223 B1 | 4/2002 | Gleason et al. |
| 6,381,349 B1 | 4/2002 | Zeng et al. |
| 6,413,998 B1 | 7/2002 | Petrie et al. |
| 6,418,189 B1 | 7/2002 | Schafer |
| 6,738,499 B1 | 5/2004 | Doi et al. |
| 2001/0010732 A1 | 8/2001 | Oosawa |
| 2001/0056099 A1 | 12/2001 | Day et al. |
| 2002/0057760 A1 | 5/2002 | Carroll et al. |
| 2002/0068864 A1 | 6/2002 | Bishop et al. |
| 2002/0172403 A1 | 11/2002 | Doi et al. |
| 2003/0142787 A1 | 7/2003 | Jabri et al. |

FOREIGN PATENT DOCUMENTS

| | | |
|---|---|---|
| EP | 0449083 | 11/1995 |
| EP | 0761166 A2 | 3/1997 |
| EP | 1005832 | 6/2000 |
| EP | 1005832 A2 | 6/2000 |
| JP | 5197813 | 6/1993 |
| WO | 95/14431 A1 | 6/1995 |
| WO | WO9526120 | 9/1995 |
| WO | 00/05678 A1 | 2/2000 |

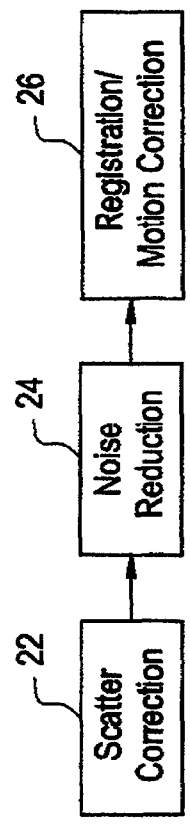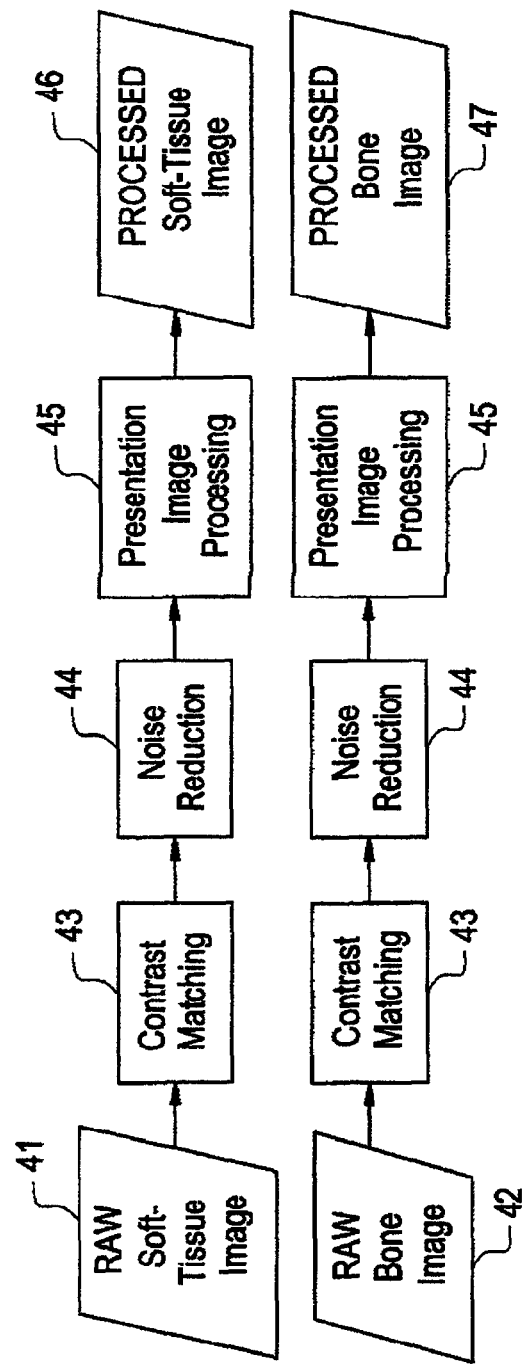

SYSTEM AND METHOD FOR COMPUTER AIDED DETECTION AND DIAGNOSIS FROM MULTIPLE ENERGY IMAGES

CROSS-REFERENCE TO RELATED APPLICATIONS

This application is a continuation of and claims priority to U.S. patent application Ser. No. 10/065,854, filed on Nov. 26, 2002, the disclosure of which is incorporated herein by reference.

BACKGROUND OF THE INVENTION

This disclosure relates generally to X-ray systems and methods, and more particularly to a system and method of determining the exposed field of view in an X-ray radiograph.

This invention generally relates to computer aided detection and diagnosis (CAD) of an image set. More particularly, this invention relates to a method and system for computer aided detection and diagnosis of dual energy ("DE") or multiple energy images, as well as of radiographic images, computed tomography images, and tomosynthesis images.

The classic radiograph or "X-ray" image is obtained by situating the object to be imaged between an X-ray emitter and an X-ray detector made of photographic film. Emitted X-rays pass through the object to expose the film, and the degree of exposure at the various points on the film are largely determined by the density of the object along the path of the X-rays.

It is now common to utilize solid-state digital X-ray detectors (e.g., an array of switching elements and photo-sensitive elements such as photodiodes) in place of film detectors. The charges generated by the X-rays on the various points of the detector are read and processed to generate a digital image of the object in electronic form, rather than an analog image on photographic film. Digital imaging is advantageous because the image can later be electronically transmitted to other locations, subjected to diagnostic algorithms to determine properties of the imaged object, and so on.

Dual energy (DE) imaging in digital X-Ray combines information from two sequential exposures at different energy levels, one with a high energy spectrum and the other with a low energy spectrum. With a digital X-ray detector, these two images are acquired sequentially and processed to get two additional images, each representative of attenuation of a given tissue type, for example bone and soft tissue images. A multiple energy imaging system can be built that can be used to further decompose the tissues in an anatomy. A series of images at different energies/kVps (Energy 1, ... Energy n) can be acquired in a rapid sequence and decomposed into different tissue types (Tissue 1, ... Tissue n).

Computed tomography (CT) systems typically include an x-ray source collimated to form a fan beam directed through an object to be imaged and received by an x-ray detector array. The x-ray source, the fan beam and detector array are orientated to lie within the x-y plane of a Cartesian coordinate system, termed the "imaging plane". The x-ray source and detector array may be rotated together on a gantry within the imaging plane, around the imaged object, and hence around the z-axis of the Cartesian coordinate system.

The detector array is comprised of detector elements each of which measures the intensity of transmitted radiation along a ray path projected from the x-ray source to that particular detector element. At each gantry angle a projection is acquired comprised of intensity signals from each of the detector elements. The gantry is then rotated to a new gantry angle and the process is repeated to collect a number of projections along a number of gantry angles to form a tomographic projection set. Each acquired tomographic projection set may be stored in numerical form for later computer processing to reconstruct a cross sectional image according to algorithms known in the art. The reconstructed image may be displayed on a conventional CRT tube, flat-panel thin-film-transistor array, or may be converted to a film record by means of a computer-controlled camera.

The fan beam may be filtered to concentrate the energies of the x-ray radiation into high and low energies. Thus, two projection sets may be acquired, one at high x-ray energy, and one at low x-ray energy, at each gantry angle. These pairs of projection sets may be taken at each gantry angle, alternating between high and low x-ray energy, such that patient movement creates minimal problems. Alternatively, each projection set may be acquired in separate cycles of gantry rotation, such that x-ray tube voltage and filtering need not be constantly switched back and forth.

Diagnosis from radiographic images, computed tomography images, and other medical images has traditionally been a visual task. Due to the subjective nature of the task, the diagnosis is subject to reader variability. In addition, due to the underlying and overlying structures relevant to the pathologies of interest, visual assessment can be difficult. Subtle rib fractures, calcifications, and metastatic bone lesions (metastases) in the chest can be difficult to detect on a standard chest X-ray. As an additional example, only 5-25% of pulmonary nodules are detected today with chest radiographs, but 35-50% are visible in retrospect. In a CT acquisition, different regions of the imaged object can be composed of different tissues of differing densities such that the total attenuation (thus CT number and pixel value) are the same. These two regions would have identical representation in the image, and thus be indistinguishable. Dual energy CT offers the ability to discriminate between the two tissue types. Traditionally, this discrimination would still be a visual task.

BRIEF DESCRIPTION OF THE INVENTION

In an embodiment, a

Various other features, objects, and advantages will be made apparent to those skilled in the art from the accompanying drawings and detailed description thereof.

BRIEF DESCRIPTION OF THE DRAWINGS

FIG. 4 is a flowchart of exemplary image pre-processing;

FIG. 5 is a flowchart of exemplary image post-processing;

DETAILED DESCRIPTION OF THE INVENTION

Figure 1:
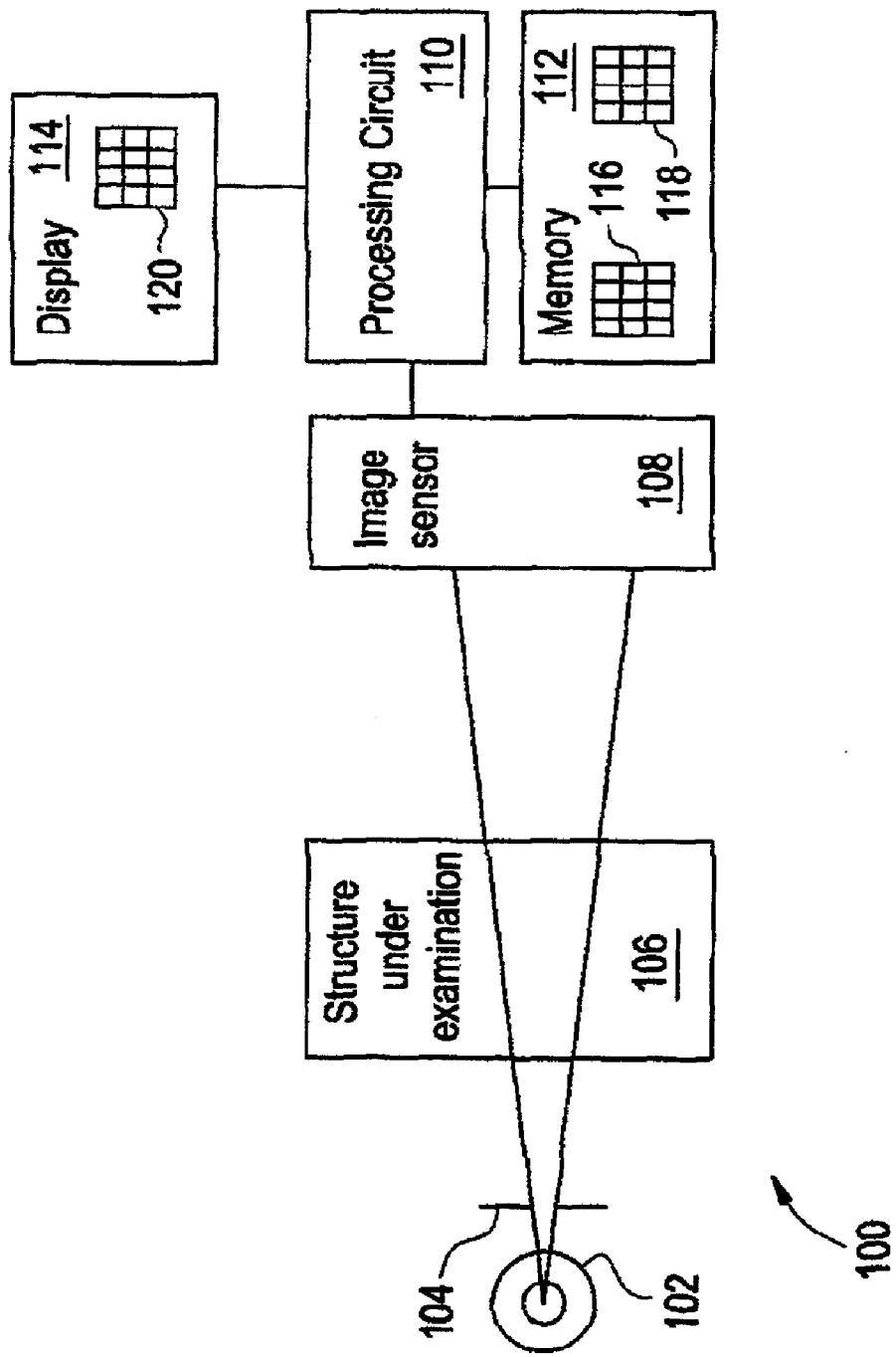
FIG. 1 is a block diagram of an exemplary X-ray imaging system.

FIG. 1 illustrates an exemplary X-ray imaging system 100. The imaging system 100 includes an X-ray source 102 and a collimator 104, which subject structure under examination 106 to X-ray photons. As examples, the X-ray source 102 may be an X-ray tube, and the structure under examination 106 may be a human patient, test phantom or other inanimate object under test. The X-ray source 102 is able to generate photons at a first energy level and at least a second energy level different than the first energy level. Multiple, more than two, energy levels are also within the scope of this method and system.

The X-ray imaging system 100 also includes an image sensor 108 coupled to a processing circuit 110. The processing circuit 110 (e.g., a microcontroller, microprocessor, custom ASIC, or the like) is coupled to a memory 112 and a display 114. The display 114 may include a display device, such as a touch screen monitor with a touch-screen interface. As is known in the art, the system 100 may include a computer or computer-like object which contains the display 114. The computer or computer-like object may include a hard disk, or other fixed, high density media dives, connected using an appropriate device bus, such as a SCSI bus, an Enhanced IDE bus, a PCI bus, etc., a floppy drive, a tape or CD ROM drive with tape or CD media, or other removable media devices, such as magneto-optical media, etc., and a mother board. The motherboard includes, for example, a processor, a RAM, and a ROM, I/O ports which are used to couple to the image sensor 108, and optional specialized hardware for performing specialized hardware/software functions, such as sound processing, image processing, signal processing, neural network processing, etc., a microphone, and a speaker or speakers. Associated with the computer or computer-like object may be a keyboard for data entry, a pointing device such as a mouse, and a mouse pad or digitizing pad. Stored on any one of the above-described storage media (computer readable media), the system and method include programming for controlling both the hardware of the computer and for enabling the computer to interact with a human user. Such programming may include, but is not limited to, software for implementation of device drivers, operating systems, and user applications. Such computer readable media further includes programming or software instructions to direct the general purpose computer to performance in accordance with the system and method. The memory 112 (e.g., including one or more of a hard disk, floppy disk, CDROM, EPROM, and the like) stores a high energy level image 116 (e.g., an image read out from the image sensor 108 after 110-140 kVp 5 mAs exposure) and a low energy level image 118 (e.g., an image read out after 70 kVp 25 mAs exposure). Processing circuit 110 provides an image 120 for display on device 114. As described in further detail herein, the image 120 may be representative of different structures (e.g., soft-tissue, bone). The image sensor 108 may be a flat panel solid state image sensor, for example, although conventional film images stored in digital form in the memory 112 may also be processed as disclosed below as well.

Figure 2:
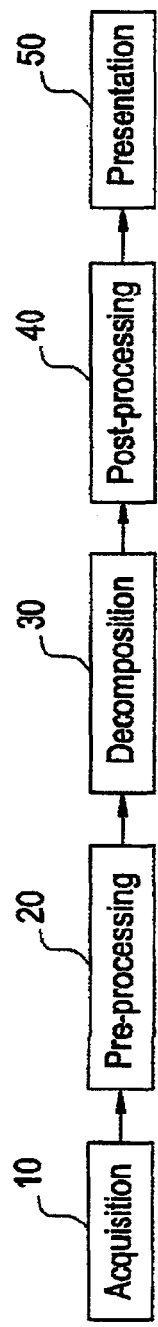
FIG. 2 is a high-level flowchart of an exemplary image acquisition and processing process.
Figure 3:
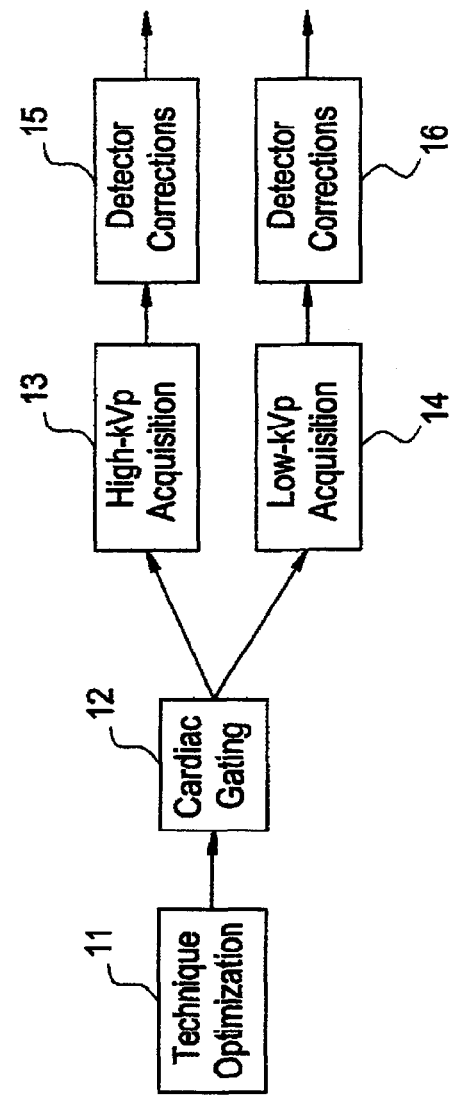
FIG. 3 is a flowchart of exemplary image acquisition processing.

Operation of the system of FIG. 1 will now be described with reference to FIGS. 2-6. FIG. 2 depicts a high-level flowchart of exemplary processing performed by the system of FIG. 1. The process begins at step 10 with image acquisition. An exemplary image acquisition routine is shown in FIG. 3. As shown in FIG. 3, the image acquisition routine includes a technique optimization step 11 that includes processing such as automatic selection of acquisition parameters such as kVp (High and Low), mAs, additional filtration (for example, copper or aluminum), timing, etc. The acquisition parameters can be based on variables provided by the user (such as patient size) or obtained automatically by the system (such as variables determined by a low-dose "pre-shot"). Selection of the acquisition parameters may address problems such as residual structures, lung/heart motion, decomposition artifacts and contrast.

Once the acquisition parameters are defined, cardiac gating is utilized at step 12. Cardiac gating is a technique that triggers the acquisition of images by detector 108 at a specific point in the cardiac cycle. This reduces heart-motion artifacts in views that include the heart, as well as artifacts indirectly related to heart motion such as lung motion. Cardiac gating addresses lung/heart motion artifacts due to heart/aortic pulsatile motion.

The acquisition of two successive x-ray images at high kVp and low kVp, with a minimum time in between, is depicted as steps 13 and 14, respectively. The filtration of collimator 104 may be changed in between acquisitions to allow for greater separation in x-ray energies. Detector corrections may be applied to both the high energy image and low energy image at steps 15 and 16, respectively. Such detector corrections are known in systems employing flat panel detectors and include techniques such as bad pixel/line correction, gain map correction, etc., as well as corrections specific to dual energy imaging such as laggy pixel corrections.

Referring to FIG. 2, once the acquisition step 10 is completed, flow proceeds to step 20 where the acquired images are pre-processed. FIG. 4 is flowchart of an exemplary pre-processing routine. The pre-processing includes a scatter correction step 22 which may be implemented in software and/or hardware. The scatter correction routine may be applied to each image individually or utilize common information from both the high kVp and the low kVp images to reduce scatter. Existing scatter correction techniques may be used such as hardware solutions including specialized anti-scatter grids, and or software solutions using convolution-based or deconvolution-based methods. Additionally, software techniques can utilize information from one image to tune parameters for the other image. Scatter correction addresses decomposition artifacts due to x-ray scatter.

Once scatter correction is performed, noise reduction is performed at step 24 where one or more existing noise reduction algorithms are applied to the high kVp and the low kVp images, either individually or simultaneously. The noise correction addresses increased noise that may result from the DE decomposition. At step 26, registration is performed to reduce motion artifacts by correcting for motion and aligning anatomies between the high kVp and the low kVp images. The registration algorithms may be known rigid-body or warping registration routines applied to the high kVp and the low kVp images. Alternatively, the techniques may be iterative and make use of the additional information in decomposed soft-tissue and bone images developed at step 30. The registration processing addresses residual structures in the soft-tissue image and/or the bone image and lung/heart motion artifacts.

Referring to FIG. 2, once the pre-processing step 20 is completed, flow proceeds to step 30 where the acquired images are decomposed to generate a raw soft-tissue image and a raw bone image. A standard image (also referred to as a standard posterior-anterior (PA) image) is also defined based on the high kVp image. The decomposition may be performed using known DE radiography techniques. Such techniques may include log-subtraction or basis material decomposition to create raw soft-tissue and raw bone images from the high-energy and low-energy acquisitions. Information from the raw soft-tissue image and raw bone image may be used in the registration/motion correction step 26. For example, edge information and/or artifact location information can be derived from the decomposed images for use in the registration/motion correction.

Referring to FIG. 2, once the decomposition step 30 is completed, flow proceeds to step 40 where the acquired images are post-processed. FIG. 5 is a flowchart of an exemplary post-processing routine. As shown in FIG. 5, the raw soft-tissue image 41 and the raw bone image 42 are subjected to similar processing. Contrast matching 43 is performed match contrast of structures in raw soft-tissue image 41 and the raw bone image 42 to the corresponding structures in a standard image. For example, contrast of soft-tissue structures in raw soft-tissue image 41 (e.g., chest image) is matched to the contrast in the standard PA image. The contrast matching is performed to facilitate interpretation of the x-ray images.

At 44, one or more noise reduction algorithms may be applied to the soft-tissue image 41 and the bone image 42. Existing noise reduction algorithms may be used. The noise reduction addresses noise due to DE decomposition. At 45, presentation image processing may be performed to the soft-tissue image 41 and the bone image 42. The presentation processing includes processes such as edge enhancement, display window level and window width adjustments for optimal display. The result of the post-processing 40 is depicted as processed soft-tissue image 46 and processed bone image 47.

Referring to FIG. 2, once the post-processing step 40 is completed, flow proceeds to step 50 where the acquired images are processed for display.

Computer-aided algorithms have the potential of improving accuracy and reproducibility of disease detection when used in conjunction with visual assessment by radiologists. Computer-aided algorithms can be used for detection (presence or absence) or diagnosis (normal or abnormal). The detection or diagnosis is performed based upon knowledge acquired by training on a representative sample database. The sample data in the database and the features of the data that the algorithms are trained are two important aspects of the training process that affect the performance of CAD algorithms. The accuracy of the CAD algorithms improves with improvements on the information it is trained on. With conventional radiographs, overlying and underlying structures confound the relevant information making diagnosis or detection difficult even for computerized algorithms. The method and system described herein addresses this problem by using dual energy images, in particular, in conjunction with conventional radiographic images for CAD. In particular, this method combines information from four images to aid computerized detection algorithms.

Figure 6:
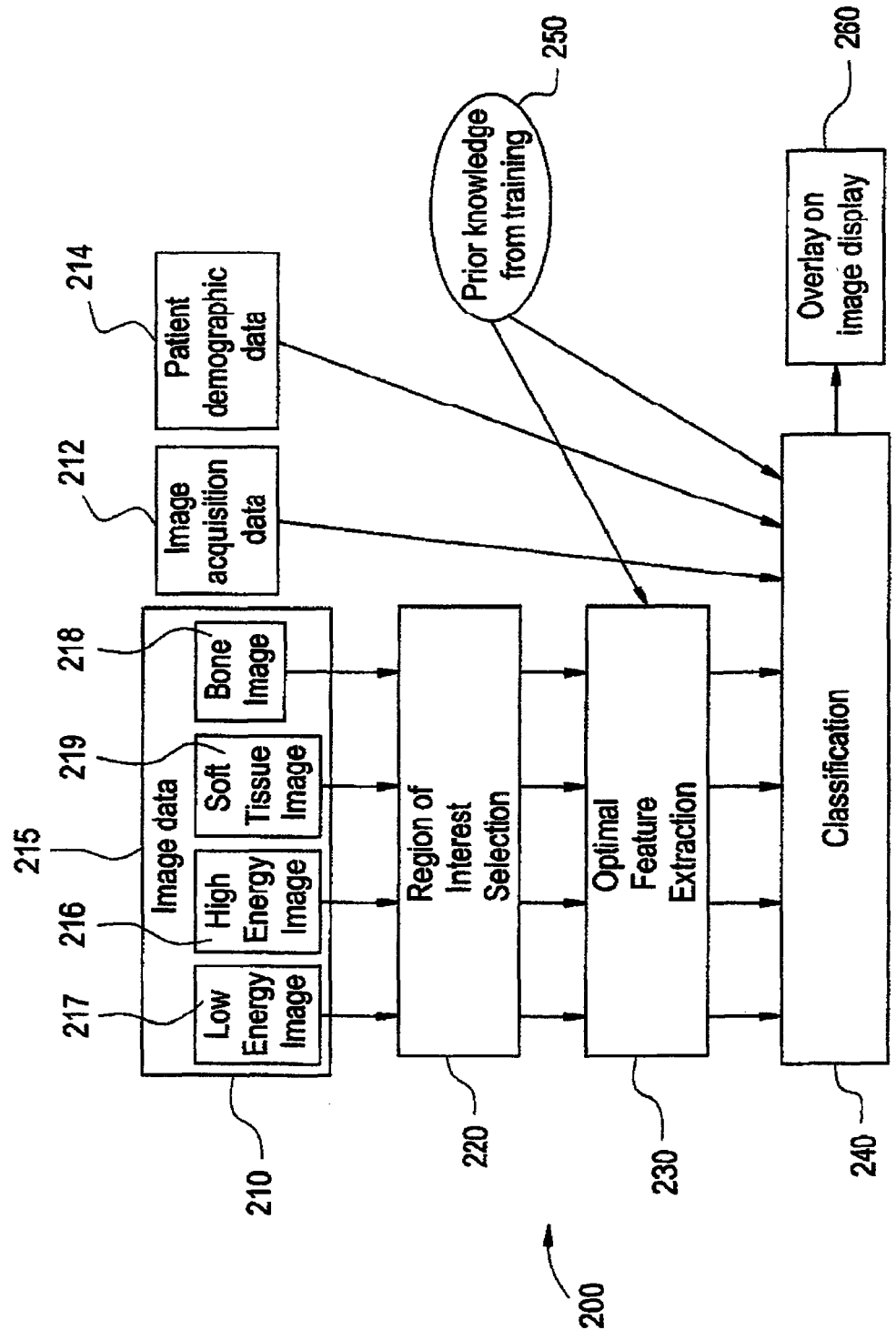
FIG. 6 is a flowchart of a computer aided process of detection and diagnosis of dual energy images.

As shown in FIG. 6 the dual energy CAD system 200 has several parts including a data source 210, a region of interest 220, optimal feature selection 230, and classification 240, training 250, and display of results 260.

Figure 7:
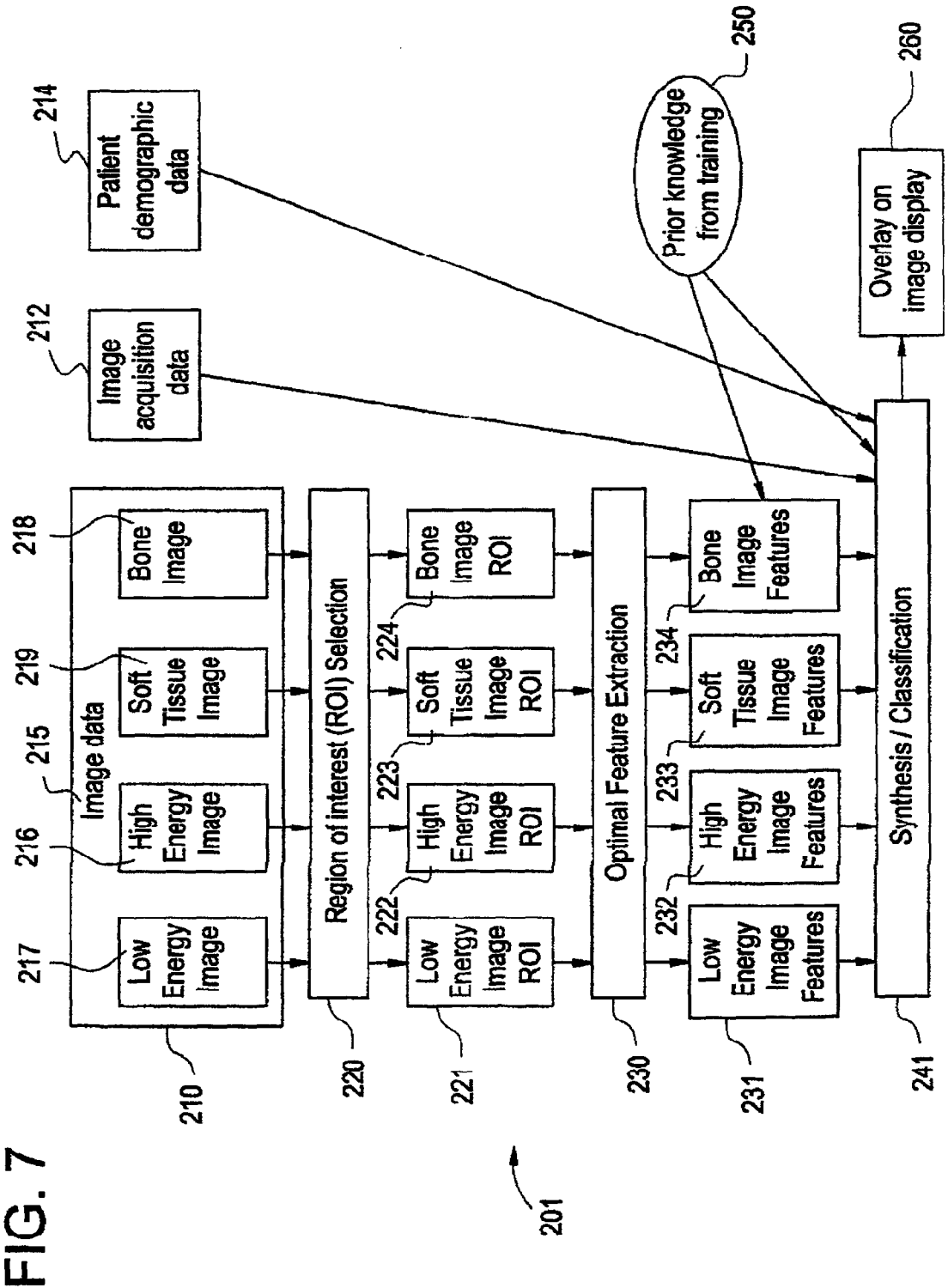
FIG. 7 is a flowchart of another computer aided process of detection and diagnosis of dual energy images.

It should be noted here that dual energy CAD 200 may be performed once by incorporating features from all images 215 or may be performed in parallel. As shown in FIG. 7, the parallel operation for a dual energy CAD 201 would involve performing CAD operations, as described in FIG. 6, individually on each image 216, 217, 218, 219 and combining the results of all CAD operations in a synthesis/classification stage 214. That is, the ROI selection 220 can be performed on each image 216, 217, 218, and 219 to provide a low energy image ROI 221, a high energy image ROI 222, a soft tissue image ROI 223, and a bone image ROI 224. Likewise, the optimal feature extraction stage 230 can be performed on each image ROI 221, 222, 223, and 224 to result in low energy image features 231, high energy image features 232, soft tissue image features 233, and bone image features 234. At the synthesis/classification stage 241, the results of all of the CAD operations can be combined. Thus, FIGS. 6 and 7 show two different methods of performing dual energy CAD, however other methods are also within the scope of this invention such as the ROI selection stage 220 performing in parallel as shown in FIG. 7, but the feature extraction stage 230 performing on a combined ROI such as shown in FIG. 6. In addition, CAD operations to detect multiple diseases, fractures, or any other medical condition can be performed in series or parallel.

Referring now to either FIG. 6 or 7, for the data source 210, data may be obtained from a combination of one or more sources. Image acquisition system information 212 such as kVp (peak kilovoltage, which determines the maximum energy of the X-rays produced, wherein the amount of radiation produced increases as the square of the kilovoltage), mA (the X-ray tube current is measured in milliamperes, where 1 mA=0.001 A), dose (measured in Roentgen as a unit of radiation exposure, rad as a unit of absorbed dose, and rem as a unit of absorbed dose equivalent), SID (Source to Image Distance), etc., may contribute to the data source 210. Patient demographics/symptoms/history 214 such as smoking history, sex age, and clinical symptoms may also be a source for data 210. Dual energy image sets 215 (high energy image 216, low energy image 217, bone image 218, soft tissue image 219, or alternatively stated, first and second decomposed images in lieu of bone image 218 and soft tissue image 219, where first and second decomposed images may include any material images including, but not limited to, soft tissue and bone images) are an additional source of data for the data source 210.

On the image-based data 215, a region of interest 220 can be defined from which to calculate features. The region of interest 220 can be defined several ways. For example, the entire image 215 could be used as the region of interest 220. Alternatively, a part of the image, such as a candidate nodule region in the apical lung field could be selected as the region of interest 220. The segmentation of the region of interest 220 can be performed either manually or automatically. The manual segmentation may involve displaying the image and a user delineating the area using, for example, a mouse. An automated segmentation algorithm can use prior knowledge such as the shape and size to automatically delineate the area of interest 220. A semi-automated method which is the combination of the above two methods may also be used.

Figure 8:
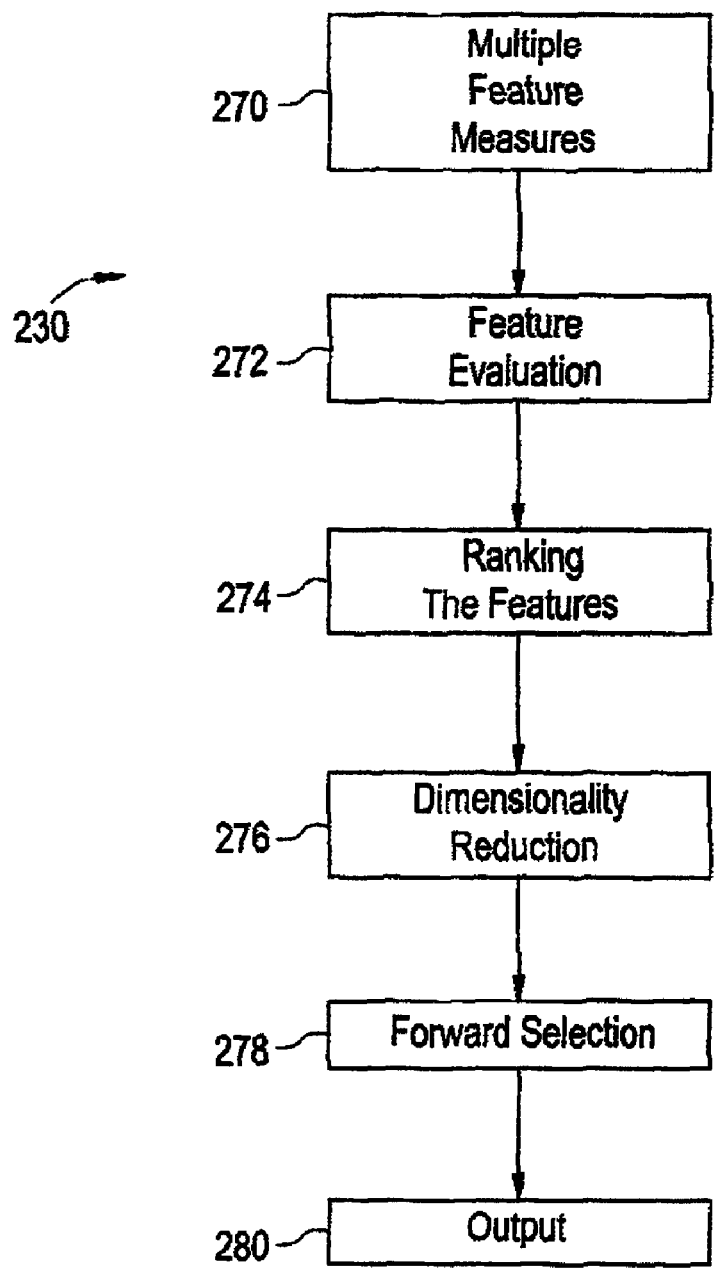
FIG. 8 is flowchart of an exemplary feature selection algorithm for use in the computer aided process of FIGS. 6 and 7.

The feature selection algorithm 230 is then employed to sort through the candidate features and select only the useful ones and remove those that provide no information or redundant information. With reference to FIG. 8, the feature extraction process, or optimal feature extraction 230, involves performing computations on the data sources 210. For example, on the image-based data 215, the region of interest statistics such as shape, size, density, curvature can be computed. On acquisition-based 212 and patient-based 214 data, the data 212, 214 themselves may serve as the features. As further shown in FIG. 8, the multiple feature measures 270 from the high energy image, low energy image, soft image, and bone images or a combination of those images are extracted, for example measured features such as shape, size, texture, intensity, gradient, edge strength, location, proximity, histogram, symmetry, eccentricity, orientation, boundaries, moments, fractals, entropy, etc., patent history such as age, gender, smoking history, and acquisition data such as kVp and dose. The term "feature measures" thus refers to features which are computed, features which are measured, and features which just exist. A large number of feature measures are included, however the method ensures that only the features which provide relevant information are maintained. Step 272 within the feature selection algorithm 230 refers to feature evaluation 272 in terms of its ability to separate the different classification groups using, for example, distance criteria. Distance criteria will evaluate how well, using a particular feature, the method can separate the different classes that are used. Several different distance criteria can be used such as divergence, Bhattacharya distance, Mahalanobis distance. These techniques are described in "Introduction to Statistical Pattern Recognition", K. Fukanaga, Academic Press, $2^{nd}$ ed., 1990, which is herein incorporated by reference. Step 274 ranks all the features based on the distance criteria. That is, the features are ranked based on their ability to differentiate between different classes, their discrimination capability. The feature selection algorithm 230 is also used to reduce the dimensionality from a practical standpoint, where the computation time might be too long if the number of features to compute is large. The dimensionality reduction step 276 refers to how the number of features are reduced by eliminating correlated features. Extra features which are merely providing the same information as other features are eliminated. This provides a reduced set of features which are used by the forward selection step 278 which selects the highest ranked features and then adding additional features, based on a descending ranking, until the performance no longer improves. That is, no more features are added when the point is reached where adding additional features no longer provides any useful information. At this point, the output 280 provides an optimal set of features.

Figure 9:
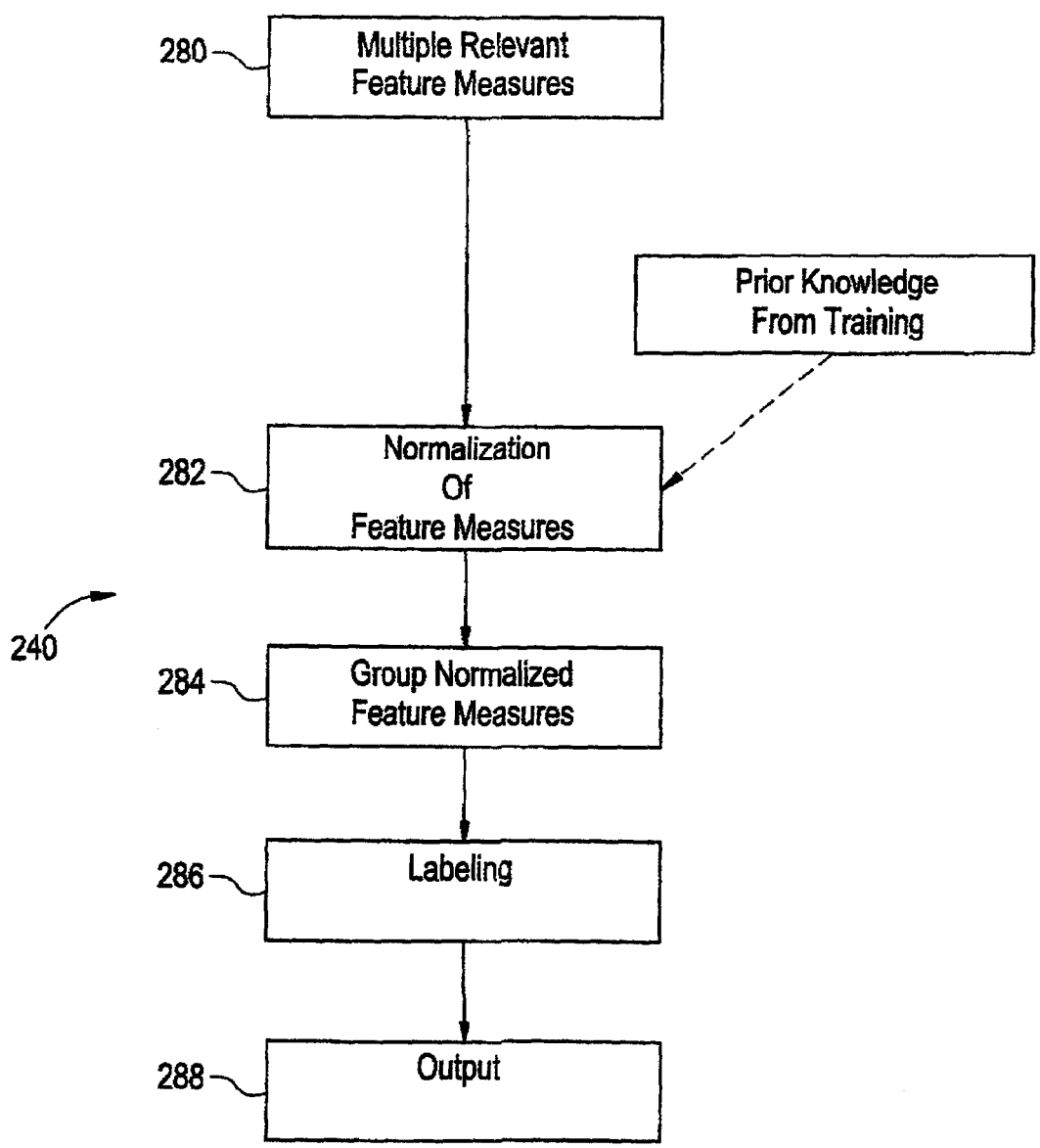
FIG. 9 is a flowchart of an exemplary classification algorithm for use in the computer aided process of FIGS. 6 and 7.

Once the features, such as shape, size, density, gradient, edges, texture, etc., are computed as described above in the feature selection algorithm 230 and an optimal set of features 280 is produced, a pre-trained classification algorithm 240 can be used to classify the regions of interest 220 into benign or malignant nodules, calcifications, fractures or metastases, or whatever classifications are employed for the particular medical condition involved. With reference to FIG. 9, the set of features 280 is used as the input to the classification algorithm 240. In step 282, the normalization of the feature measures from set 280 is performed with respect to feature measures derived from a database of known normal and abnormal cases of interest. This is taken from the prior knowledge from training 250. The prior knowledge from training may contain, for example, examples of features of confirmed malignant nodules and examples of features of confirmed benign nodules. The training phase 250 may involve, for example, the computation of several candidate features on known samples of benign and malignant nodules. Step 284 refers to grouping the normalized feature measures. Several different methods can be used such as Bayesian classifiers (an algorithm for supervised learning that stores a single probabilistic summary for each class and that assumes conditional independence of the attributes given the class), neural networks (which works by creating connections between processing elements whereby the organization and weights of the connections determine the output; neural networks are effective for predicting events when the networks have a large database of prior examples to draw on, and are therefore useful in image recognition systems and medical imaging), rule-based methods (which use conditional statements that tells the system how to react in particular situations), fuzzy logic (which recognizes more than simple true and false values), clustering techniques, and similarity measure approach. Such techniques are described in "Fundamentals of Digital Image Processing" by Anil K. Jain, Prentice Hall 1988, herein incorporated by reference. Once the normalized feature measures have been grouped, then the classification algorithm 240 labels the feature clusters in step 286 and outputs in step 288 a display of the output.

Dual-energy techniques enable the acquisition of multiple images for review by human or machine observers. CAD techniques could operate on one or all of the images 216, 217, 218, and 219, and display the results 260 on each image 216, 217, 218, and 219, or synthesize the results for display 260 onto a single image 215. This would provide the benefit of improving CAD performance by simplifying the segmentation process, while not increasing the quantity of images to be reviewed. This display of results 260 forms part of the presentation phase 50 shown in FIG. 2.

Following identification 230 and classification 240 of a suspicious candidate region, its location and characteristics should be displayed to the radiologist or reviewer of the image. In non-dual-energy CAD applications this is done through the superposition of a marker, for example an arrow or circle, near or around the suspicious lesion. Dual-energy CAD affords the ability to display markers for computer detected (and possibly diagnosed) nodules on any of the four images (high energy image 216, low energy image 217, bone image 218, soft tissue image 219). In this way, the reviewer may view only a single image 215 upon which is superimposed the results from an array of CAD operations 200. The CAD system 201 synthesizes the results in step 241 when the images are processed separately as shown in FIG. 7. Each CAD operation (defined by a unique segmentation (ROI) 220, feature extraction 230, and classification procedure 240 or 241) may be represented by a unique marker style.

An example of such a dual energy CAD display will be described for lung cancer chest imaging. Let us assume that a patient has a dual-energy exam (as described with reference to FIGS. 1-5) that is then processed with a dual-energy CAD system 200 or 201. A CAD operation identifies two suspicious lesions characteristic of malignancy on the soft-tissue image 219. On the bone-image 218, a CAD operation identifies a calcified nodule (indicating a benign process), and a bone lesion. At the synthesis stage, which may form part of the classification process when either or both of the ROI and feature extraction stages apply to each image, the classification 240 takes these results and determines that one of the soft-tissue nodules is the same as the calcified nodule apparent on the bone-image 218. The reviewer would then be presented with the high energy image 216, a first image—taken with a technique to mimic what is currently standard practice for single-energy chest radiography. The reviewer would also be presented with a second image, the same image as the first image but with markers indicating the results of the CAD operations 220, 230, 240 superimposed on the image data. This second image could be simultaneously displayed on a second hard- or soft-copy image display, or toggled with the other images via software on a soft-copy display. Superimposed upon the second image may be, for example, circles around the suspicious lung nodule classified as having characteristics of malignancy, a square around the calcified lung nodules classified as benign, and an arrow pointing to the detected bone lesions. In this manner, the reviewer gets the benefit of the information from CAD operations 200 on each image presented simultaneously for optimal review.

As another example, the methods 200, 201 may be used in mammography. Dual energy imaging for mammography has been previously employed, such as described in U.S. Pat. No. 6,173,034 to Chao. Advantageously, the methods 200, 201 may take the results of a dual energy imaging process performed for mammography and employ the CAD techniques as described herein. Also, it should be noted that the energies employed in mammography may be as low as 20 kVp as opposed to the energies employed typically in the above-described chest exam which may be in the range of 50-170 kVp. Conventional mammographies are typically 24-30 kVp, and DE mammographies can be 24-30 kVp for the low energy image and 50-80 kVp for the high energy image, where values are often limited by the x-ray tube/generator. For CT mammographies, the energies may be higher, about 80 kVp for a conventional single energy image.

These methods 200, 201 improve the performance of computer-aided detection or diagnosis algorithms by providing input data with overlying structures removed. Also, since the imaged anatomy is separated based on tissue type (soft tissue or bone), this algorithm 200 has the potential of extracting more diagnostic features per anatomy than with standard radiography.

Previous CR (computed radiography) dual-energy images are of rather poor quality and noisy compared to the standard radiology image and thus computer-aided algorithms have not been previously employed on such images. This system and method 200, 201 uses information from high energy image 216, low-energy image 217, soft-tissue image 219, and bone images 218 in addition to acquisition parameters 212 and patient information 214. Furthermore, the results can be displayed to the reviewer without increasing the number of images over that of conventional CAD techniques.

The above-described methods 200, 201 can additionally be utilized for identification of calcifications, bone fractures, bone erosions, and metastatic bone lesions. By providing a bone image 218 with no over/underlying soft-tissue, DE imaging creates an effective opportunity for automatic detection and classification of subtle bone fractures, bone erosions, calcifications and metastases that might otherwise be missed by the standard image reader.

Figure 10:
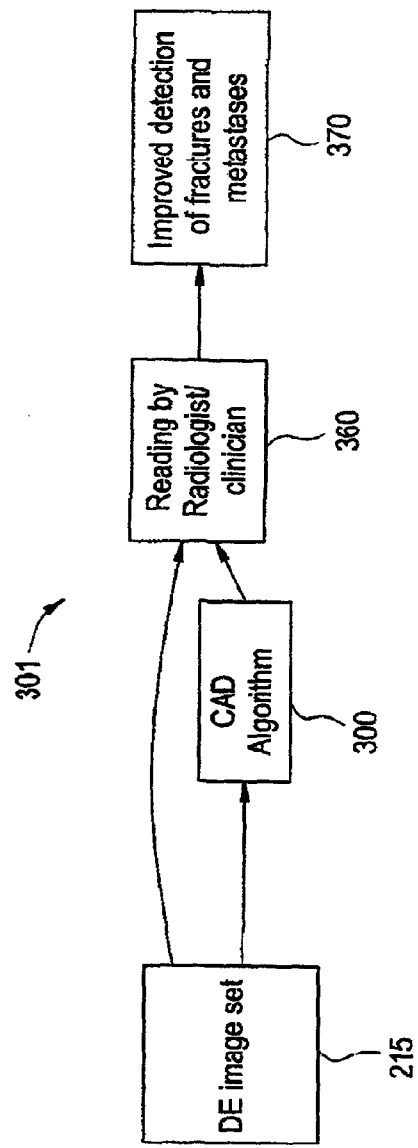
FIG. 10 is a flowchart of a computer aided process of detecting calcifications, fractures, erosions, and metastases in a bone image.
Figure 11:
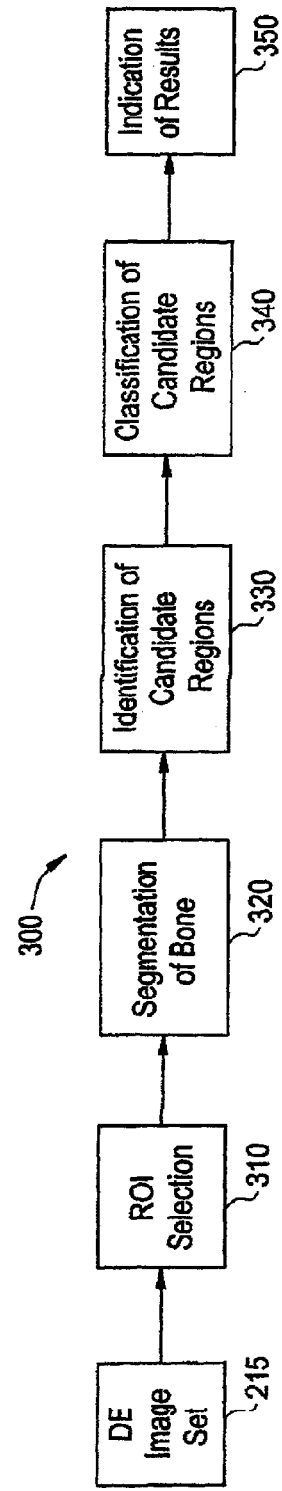
FIG. 11 is a flowchart of a computer aided algorithm for use in the process of FIG. 10.

Turning now to FIGS. 10 and 11, a diagrammed example of the methods 200, 201 is shown. The method 301 uses a dual energy computer-aided detection/diagnosis (CAD) algorithm 300 for segmenting the bone from the background and detecting/identifying candidate bone regions with possible calcifications, fractures or metastases. These candidate regions are then classified based on features extracted from the corresponding complete image set 215 (high-energy 216, low-energy 217, bone 218, and soft-tissue 219). The classification stage not only rules out what it considers false positives, but can also provide additional information about the fracture or lesion (fracture type, lesion size, etc.) The results are then highlighted on the images for the reader to assess.

As shown in FIG. 11, the first step in a CAD algorithm 300 for detecting calcifications, bone fractures, bone erosions, and metastases in DE images 215 requires the selection of the desired area to search, or selection of the region of interest (ROI) 310. In a dual energy chest exam, this would typically include the entire image, but may include a smaller region of interest if a specific region were suspected. The selection of the region of interest (ROI) 310 can be done manually or by automated algorithms based on user specifications as described above with reference to ROI 220.

Next, segmentation of bone 320 occurs. The purpose of the segmentation 320 is to separate the bone from the background (non-bone). One embodiment would be a region-growing algorithm. Manual or automated methods can be used for initializing region growing. In manual methods, a means is provided for the user to select the seed point(s). In automated methods, attributes of the bone such as intensity range, gradient range, shape, size etc. can be used for initializing seed points. Another potential segmentation method would involve multi-level intensity thresholding.

Then, candidate regions can be identified in step 330. One method for identifying candidate regions is based on an edge detection algorithm. To eliminate noise and false edges, image processing using morphological erosion could follow. In addition, to rule out longer lines that are most likely rib edges, a connectivity algorithm could be applied. Therefore, the remaining image consists of only those edges that are possible candidates for the calcifications, fractures and metastases.

Candidate regions may then be classified in step 340. The classification of the remaining candidate regions may comprise a rule-based approach. The rules can be different for identification of calcifications, metastases and fractures. There will preferably be different rules for the different types of fractures, and different rules for the different properties of metastases. For example, for fractures, one might wish to separate the edges inside the ribs from the edges outside the ribs, as edges inside the ribs are candidates for fractures. Rules could also be based on size measurements of the line edges.

Remaining candidate regions should then be indicated to the user or reader for inspection in a presentation step, or indication of results 350. This could be performed by highlighting areas on the original bone image, either with arrows, circles, or some other indicator or marker. Additional information such as lesion type or size can also be overlaid on the images.

Referring again to FIG. 10, the indication of results 350 may then be read by a radiologist or clinician in step 360 and this method 301 can be used to improve the detection of calcifications, subtle rib fractures, subtle bone erosions, and metastatic bone lesions in chest radiography as exemplified by step 370. The detection of such ailments can lead to increased benefit to the patient by early detection, leading to improved patient care by the clinician. The ability to provide a bone image without over/underlying soft-tissue can also be used to greatly improve detection and diagnosis of bone-related pathology. Using the bone image for calcifications, fracture and metastases detection is a diagnostic concept for DE imaging which has not previously been available.

While specific examples including lung cancer chest imaging and detection of calcifications, bone fractures, bone erosions, and metastases have been described, it should be understood that the methods and systems described above could be employed for detecting and/or diagnosing any medical condition, obstruction, or disease involving any part of the body.

Figure 12:
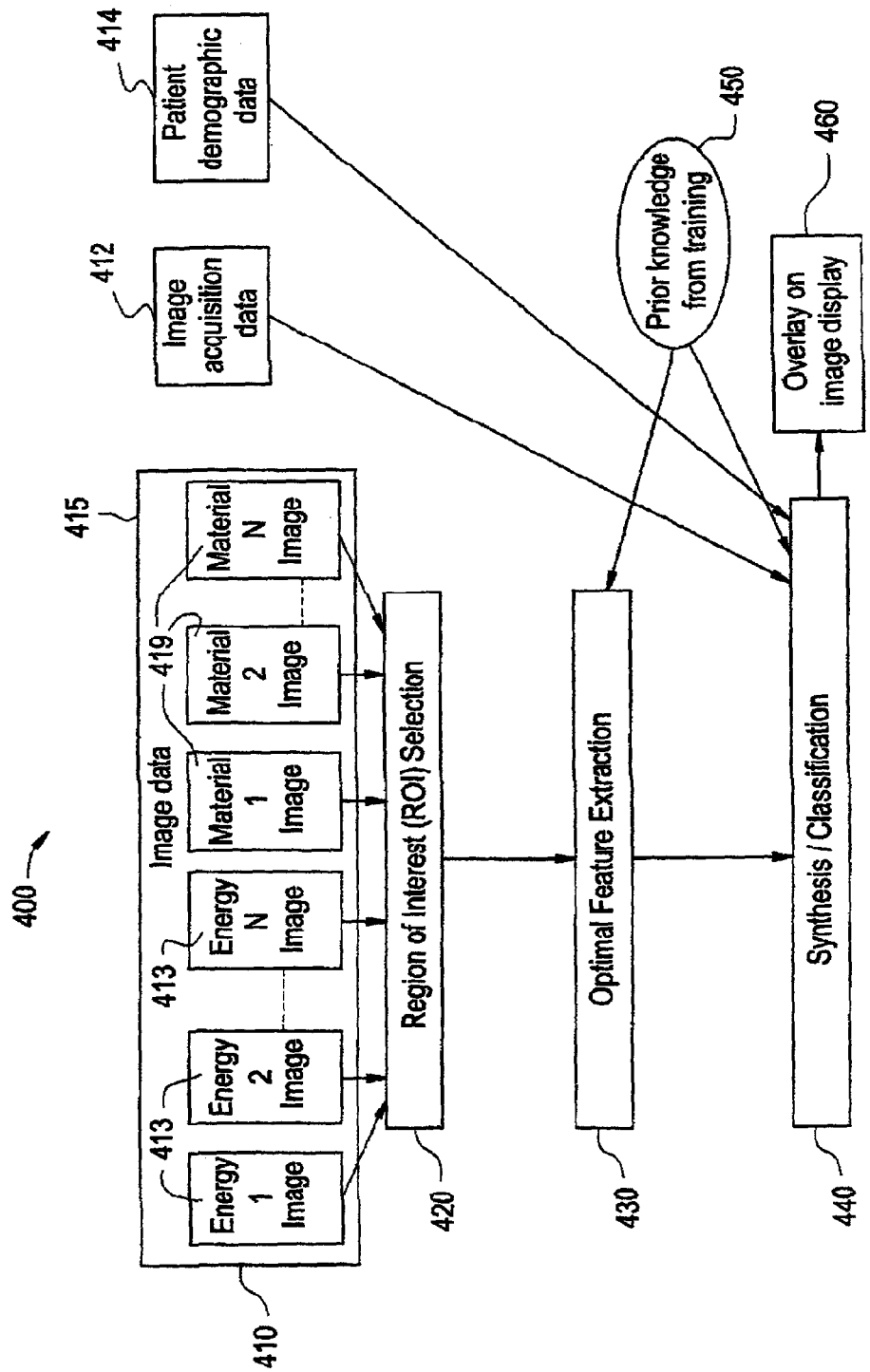
FIG. 12 is a flowchart of a computer aided process of detection and diagnosis of multiple energy images.

Also, while DE imaging has been specifically addressed, it is further within the scope of this invention to employ the above-described methods on multiple energy images. For example, a multiple energy imaging system 400 is shown in FIG. 12, which is similar to the DE imaging systems 200, 201, and 300 as described above in that in includes a data source 410 including image data 415, image acquisition data 412, and patient demographic data 414, defining or selecting a region of interest 420, optimal feature extraction 430, synthesis/classification 440, and overlay on image display 460. Also as in the previously described DE imaging systems, prior knowledge from training 450 is applied to the optimal feature extraction stage 430 and the synthesis/classification stage 440. Thus, the only distinction between the method 400 and the previously described DE methods is the content of the image data 415. That is, while the DE methods utilize a high energy image, a low energy image, a soft tissue image and a bone image, the multiple energy imaging system 400 uses a series of images 413 taken at different energies/kVps (Energy 1 image, Energy 2 image, . . . Energy N image). It should be noted that "N" denotes an arbitrary number and may change from one imaging process to the next. While these images 413 can be acquired in a rapid sequence and decomposed into a bone image 418 and different tissue type images, they may also be decomposed into different material images (material 1 image, material 2 image, . . . material N image) which may or may not include a bone image. Information from one or more of these images can be used to detect and diagnose various diseases or medical conditions. As an example, if a certain disease needs to be detected, regions of interest can be identified and features can be computed on material 2 image and the Energy 1 image. For a different disease type, all the images may be used. As in the DE energy imaging systems, region of interest selection, optimal feature computation, and classification may be performed in series or in parallel on the image data 415. For the purposes of this specification, it should further be noted that "multiple" energy imaging may encompass dual energy imaging, since two images are multiple images.

Figure 13:
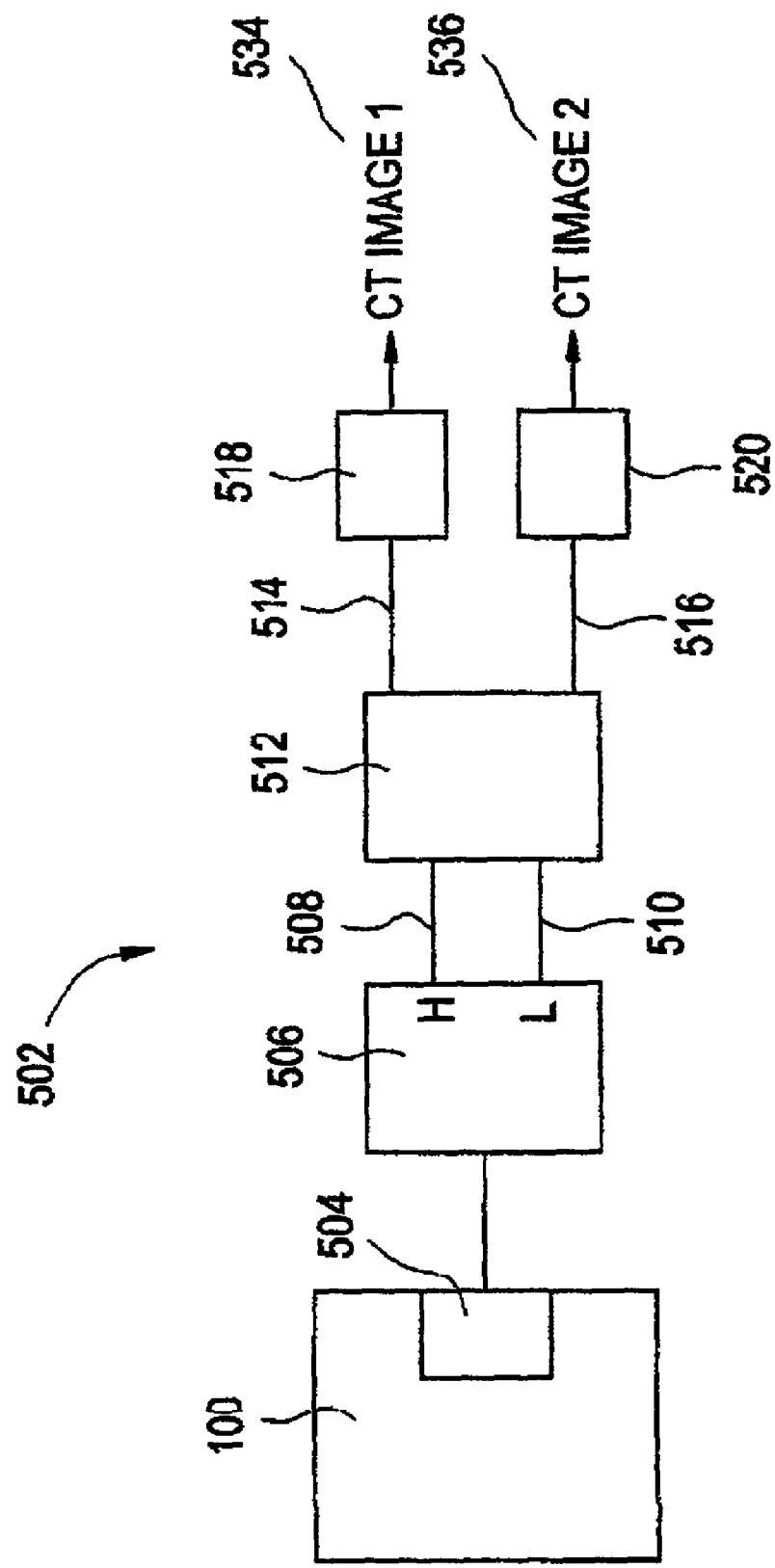
FIG. 13 is a signal flow diagram of a system capable of performing pre-reconstruction analysis.
Figure 14:
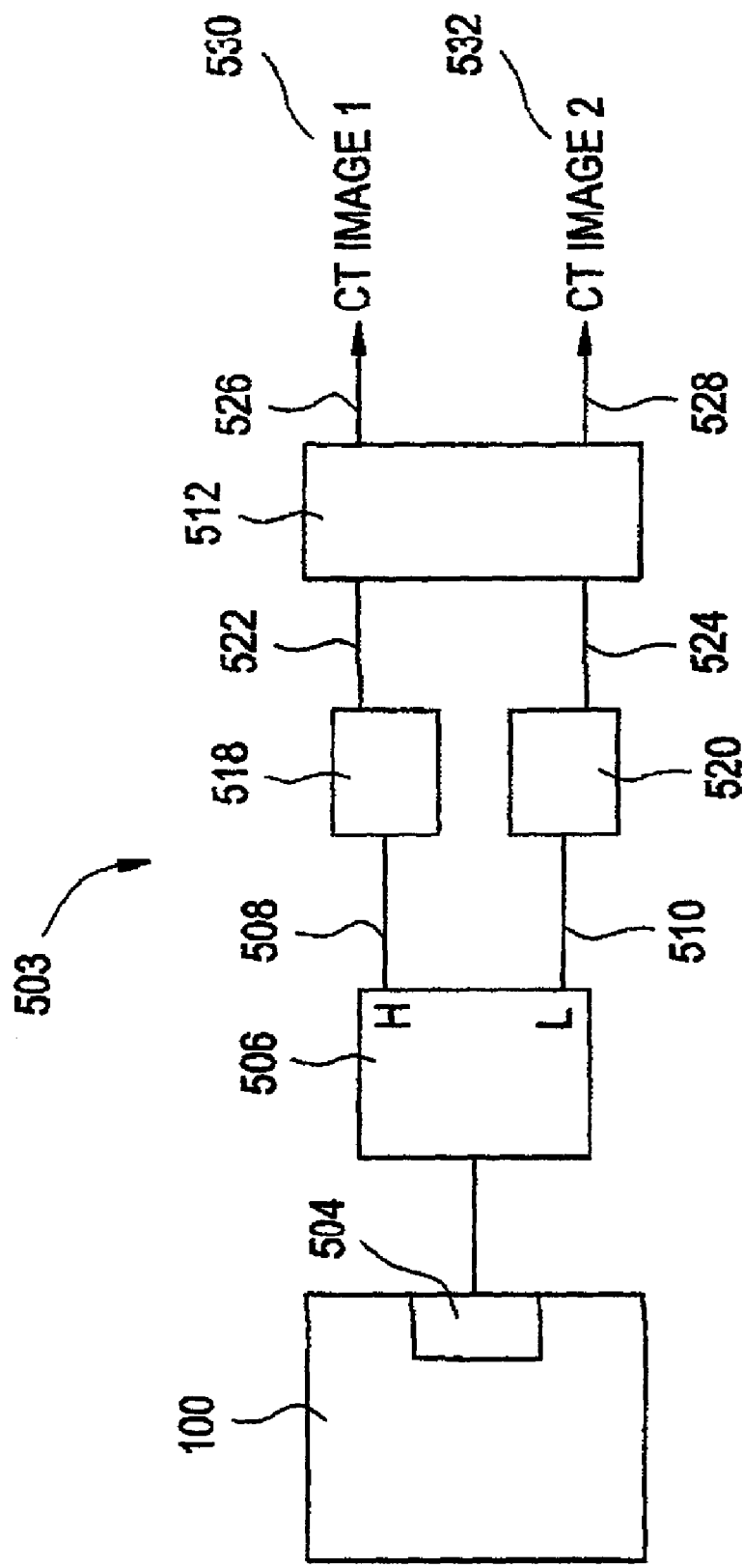
FIG. 14 is a signal flow diagram of a system capable of performing post-reconstruction analysis.

The CAD system and methods described above may further extend to dual or multiple energy computed tomography. Referring to FIGS. 13 and 14, pre-reconstruction analysis and post-reconstruction analysis are prior art techniques generally recognized for using dual energy X-ray sources in materials analysis. In pre-reconstruction analysis 502, the signal flow is as shown in FIG. 13. The system 100 is typically similar to the one shown in FIG. 1 and has an X-ray source capable of producing a fan beam at two distinct energy levels (i.e., dual energy). The data acquisition system 504 gathers signals generated by detector array at discrete angular positions of the rotating platform (not shown) and passes the signals to the pre-processing element 506. The pre-processing element 506 re-sorts the data it receives from the data acquisition system 504 in order to optimize the sequence for the subsequent mathematical processing. The pre-processing element 506 also corrects the data from the data acquisition system 504 for detector temperature, intensity of the primary beam, gain and offset, and other deterministic error factors. Finally, the pre-processing element 506 extracts data corresponding to high-energy views and routes it to a high energy channel path 508, and routes the data corresponding to low-energy views to a low energy path 510. The projection computer 512 receives the projection data on the high energy path 508 and the low energy path 510 and performs Alvarez/Macovski Algorithm processing to produce a first stream of projection data 514 which is dependent on a first parameter of the material being scanned and a second stream of projection data 516 which is dependent on a second parameter of the material scanned. The first parameter is often the atomic number and the second parameter is often material density, although other parameters may be selected. A first reconstruction computer 518 receives the first stream of projection data 514 and generates a CT image from the series of projections corresponding to the first material parameter. A second reconstruction computer 520 receives the second stream of projection data 516 and generates a CT image from the series projections corresponding to the second material parameter.

In post-reconstruction analysis 503, the signal flow is as shown in FIG. 14. As is described herein for pre-processing analysis 502, a pre-processing element 506 receives data from a data acquisition system 504, performs several operations upon the data, then routes the data corresponding to high-energy views to a high energy path 508 and routes the data corresponding to low-energy views to a low energy path 510. A first reconstruction computer 518 receives the projection data from the high energy path 508 and generates a CT image corresponding to the high-energy series of projections. A second reconstruction computer 520 receives the projection data fro the low-energy path 510 and generates a CT image corresponding to the low-energy series of projections. A projection computer 512 receives the high energy CT data 522 and the low-energy CT data 524 and performs basis material decomposition to product CT data 526 which is dependent on a first parameter of the material being scanned and a second stream of projection data 528 which is dependent on a second parameter of the material scanned.

Figure 15:
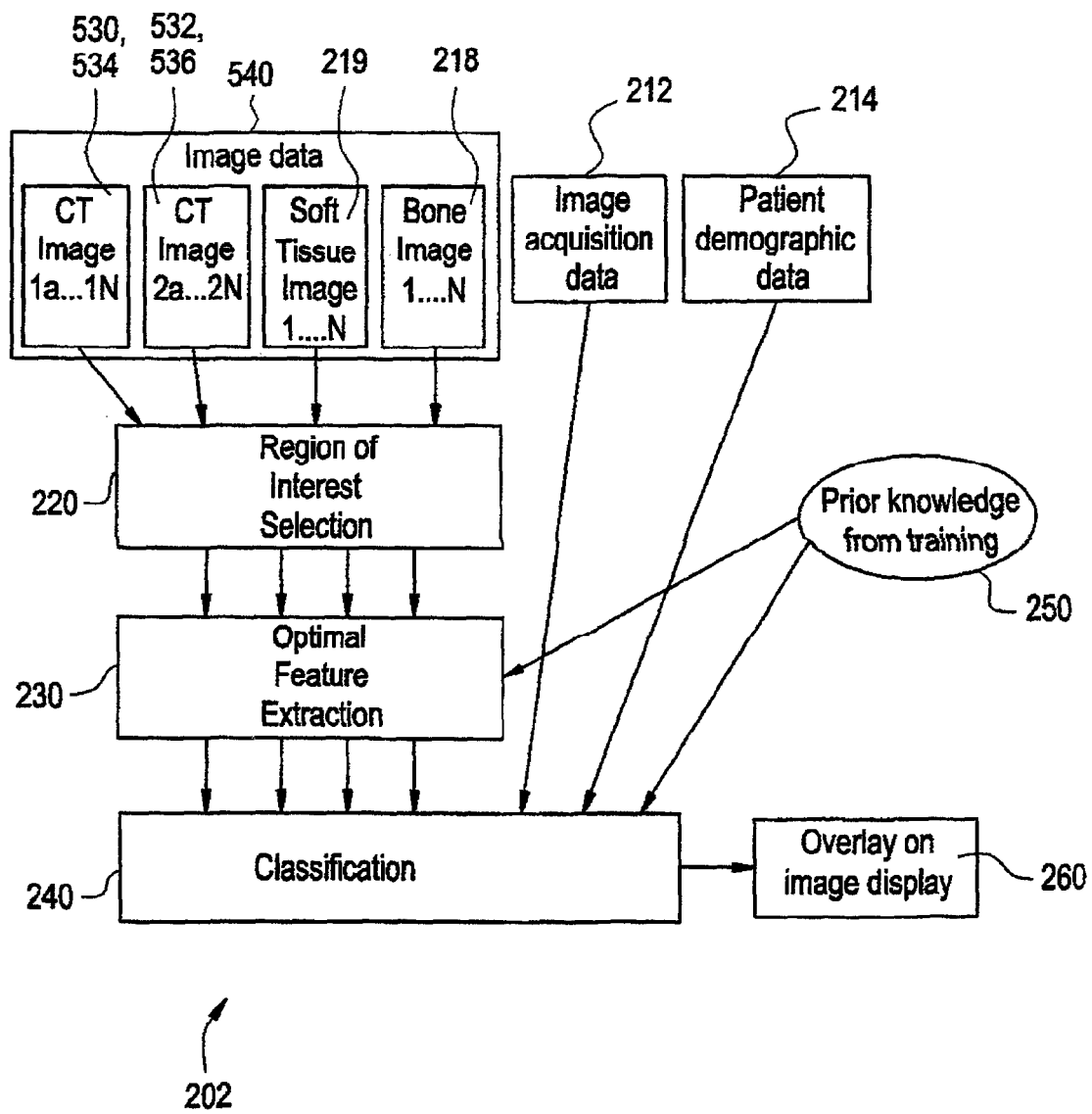
FIG. 15 is a flowchart of a computer aided process of detection and diagnosis of dual energy CT images.

FIG. 15 shows the method of computer aided detection and diagnosis 202 revised for dual energy CT imaging. The method 202 is similar to the method 200 described with respect to FIG. 6, except that multiple CT images 1a, . . . 1N 530 or 534 and multiple CT images 2a, . . . 2N 532 or 536, as described above with respect to either FIG. 13 or 14, replace high energy image 216 and low energy image 217 to form image set 540. It should be understood that "N" may denote any arbitrary number and need not be the same number as the "N" in FIG. 12. It should also be understood that while soft tissue image 219 and bone image 218 are shown, the image data 540 could instead include first decomposed images and second decomposed images, as previously described with respect to FIG. 6. Also, it should be understood that the CAD method 201 shown in FIG. 7 could also be revised for dual energy CT.

Also, the embodiment shown in FIG. 15 could be revised for volume CT where images of a structure are collected from multiple angles. Volume CT, or cone-beam CT, is a three-dimensional extension of the more familiar two-dimensional fan-beam tomography. In fan-beam tomography, a fan collection of X-rays are generated by placing a collimator with a long and narrow slot in front of a point X-ray source. A cone-beam family of x-rays is made by removing the collimator. This allows the x-rays to diverge from the point x-ray source to form a cone-like solid angle. A divergent line integral data set results when the x-rays, which penetrate the object, are collected by a detector located on the opposite side. Cone-beam tomography involves inverting the cone-beam data set to form an estimate of the density of each point inside the object.

Figure 16:
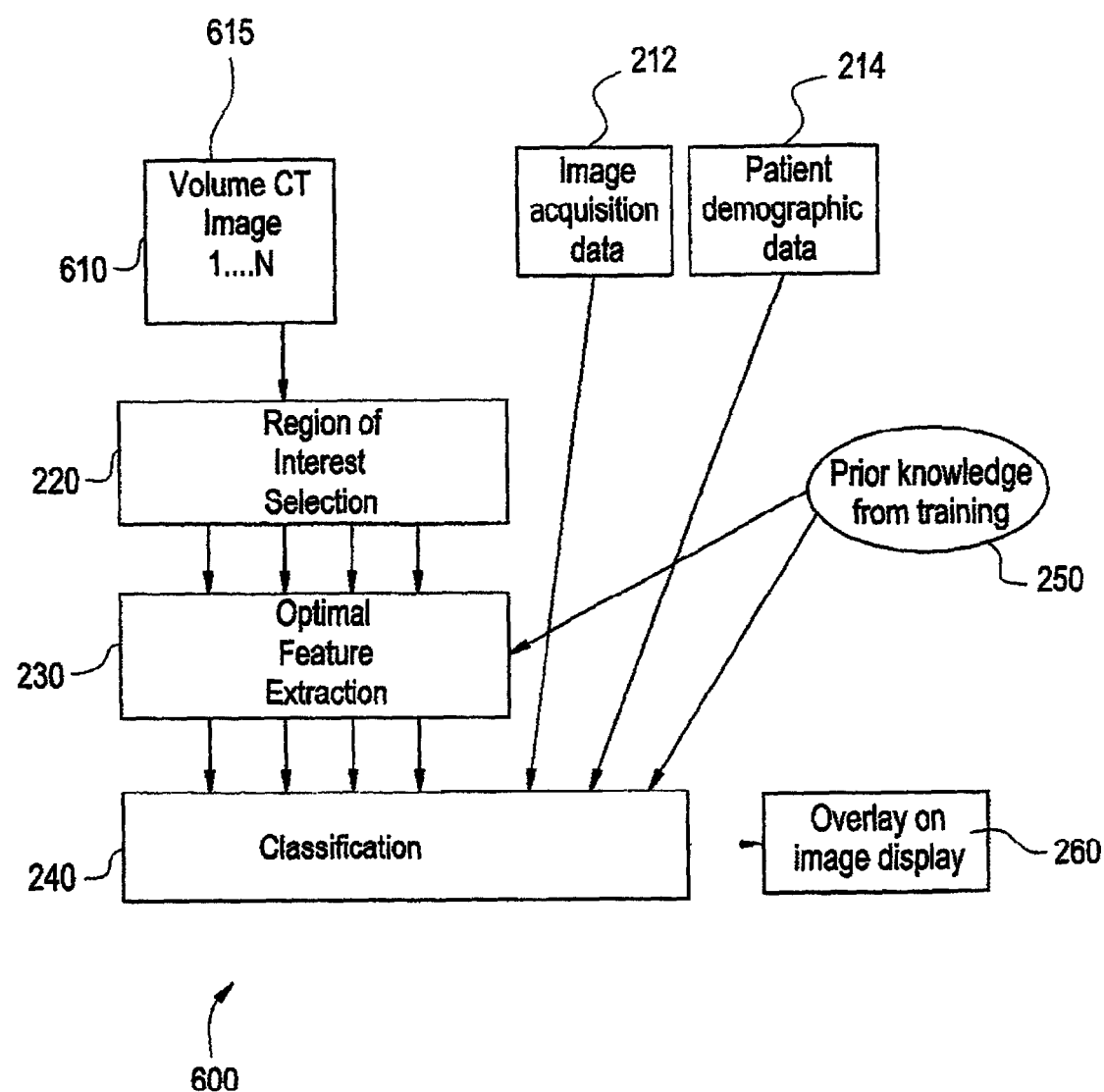
FIG. 16 is a flowchart of a computer aided process of detection and diagnosis of volume CT images.

In current CT scanners, a series of axial images of the object are made and stacked on top of each other to form the 3D object. In multi-slice CT, multiple detectors are used to collect multiple slices at a given time. On the other hand, in cone-beam tomography, the entire data is collected in parallel and then reconstructed. Therefore, the cone-beam tomography, in theory, improves both the spatial and temporal resolution of the data. FIG. 16 shows a CAD system 600 which uses Volume CT images 1 . . . N for image data 615 such that data source 610 includes volume CT images 615, image acquisition data 212, and patient demographic data 214. Otherwise, the CAD system is similar to system 200 described with respect to FIG. 6. Alternatively, the operations 220. 230, 240 may be performed in parallel on each volume CT image as described with respect to FIG. 7.

Figure 17:
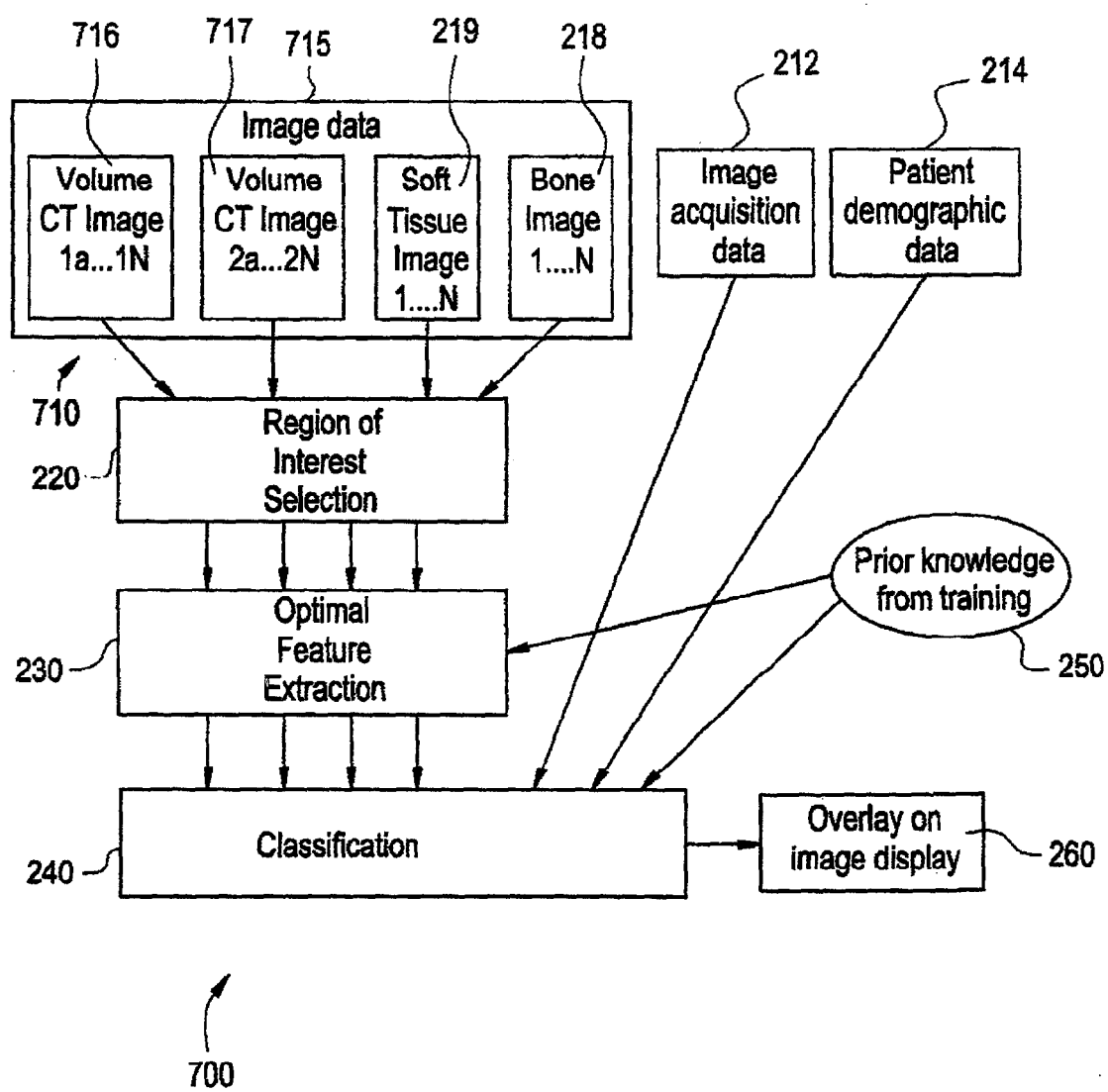
FIG. 17 is a flowchart of a computer aided process of detection and diagnosis of dual energy volume CT images.

In another embodiment, as shown in FIG. 17, a dual energy CAD system 700 uses high and low energy Volume CT images $1a$ . . . 1N 716 and $2a$ . . . 2N 717, respectively, as well as soft tissue images 1 . . . N 219 and bone images 1 . . . N 218 (or alternatively first decomposed images and second decomposed images) as image data 715, such that data source 710 includes image data 715, image acquisition data 212, and patient demographic data 214. Otherwise, the CAD system 700 is similar to system 200 described with respect to FIG. 6. Alternatively, the operations 220, 230, 240 may be performed in parallel on each Volume CT image and each soft tissue image and bone image as described with respect to FIG. 7.

While Volume CT CAD 600 and DE Volume CT CAD 700 are described in FIGS. 16 and 17, it is further contemplated that multiple energy Volume CT CAD may be employed using the methods described with respect to FIG. 12, that is, the method shown in FIG. 17 may be expanded to incorporate additional energies.

Figure 18:
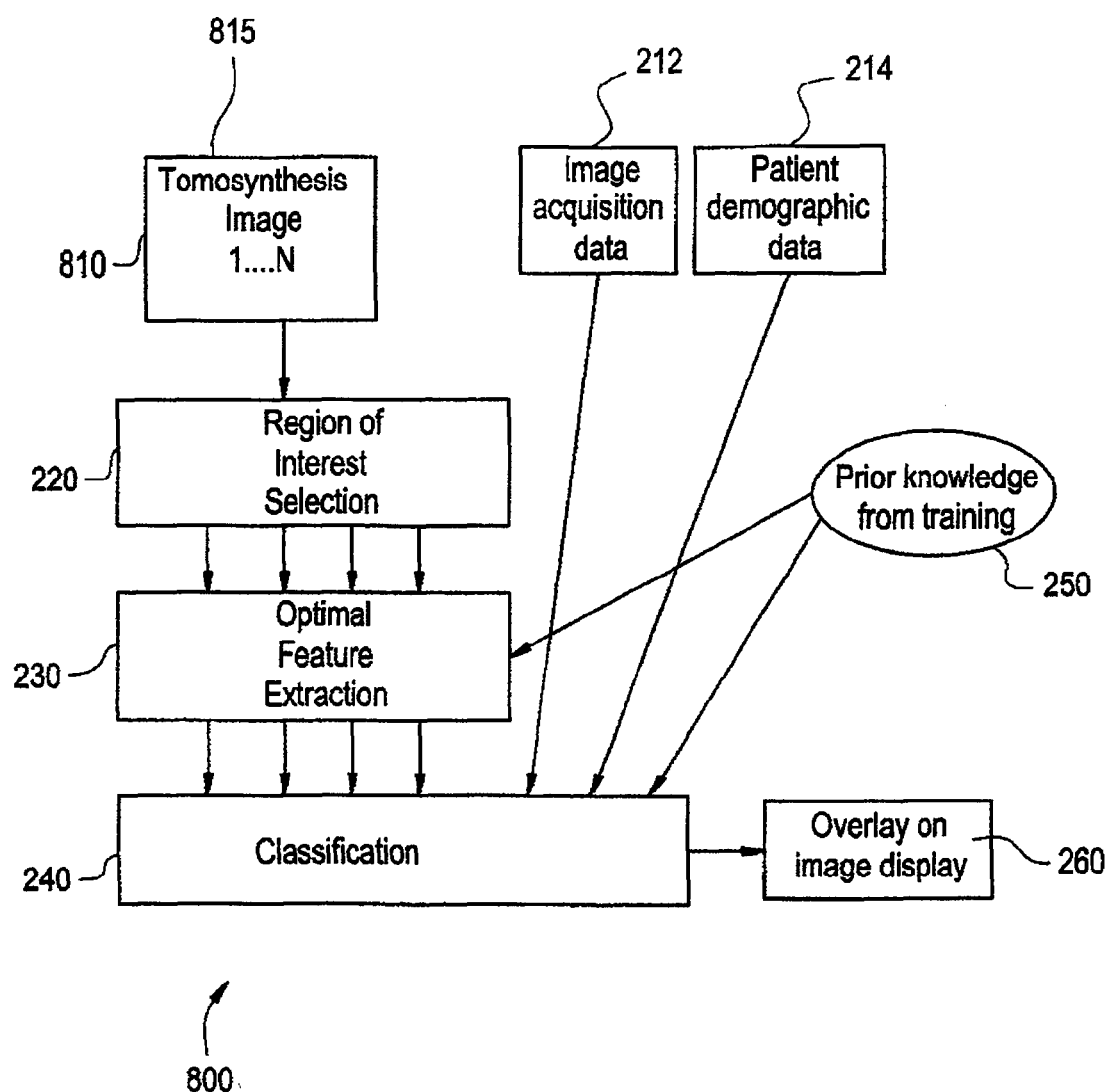
FIG. 18 is a flowchart of a computer aided process of detection and diagnosis of tomosynthesis images.

As an alternative embodiment, an imaging mode where limited angle x-ray tomosynthesis acquisition is performed and reconstructed may be combined with the computer aided detection and diagnosis methods described above and as shown in FIG. 18. Tomosynthesis is performed by acquiring multiple images with a digital detector, i.e. series of low dose images used to reconstruct tomography images at any level. Tomosynthesis may be performed using many different tube motions including linear, circular, elliptical, hypocycloidal, and others. In tomosynthesis, image sequences are acquired, with typical number of images ranging from 5 to 50. Thus, the imaging portion of this embodiment may be less expensive, although not necessarily preferred, over the CAD CT methods described above. The tomosynthesis CAD system 800 shown in FIG. 18 is similar to the CT CAD system shown in FIG. 16 except that the image data 815 includes tomosynthesis images 1 . . . N, such that data source 810 includes tomosynthesis images 815, image acquisition data 212, and patient demographic data 214. Other than data source 810, the system 800 is similar to system 200 described with respect to FIG. 6. Alternatively, the operations 220, 230, 240 may be performed in parallel on each tomosynthesis image as described with respect to FIG. 7.

Figure 19:
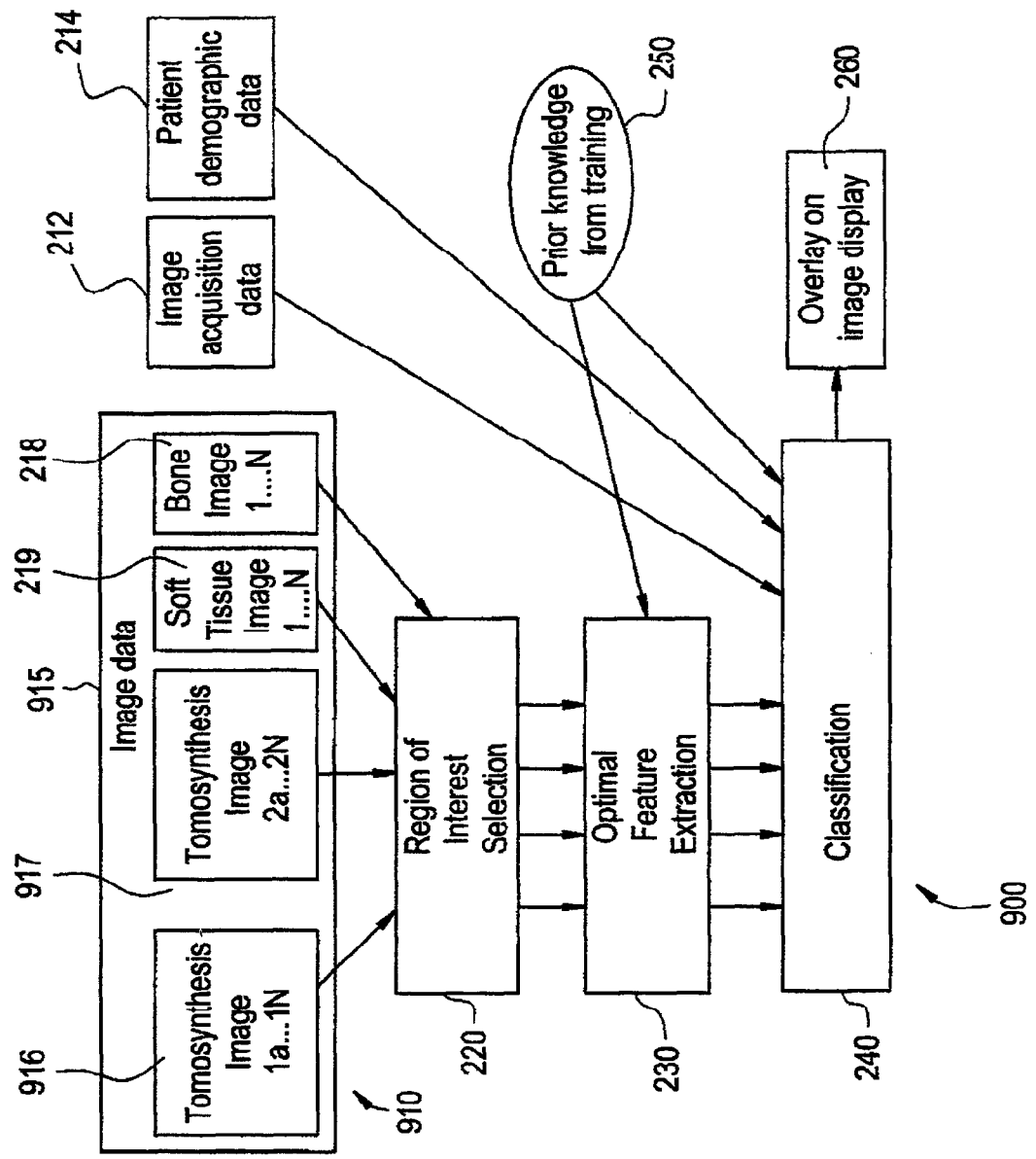
FIG. 19 is a flowchart of a computer aided process of detection and diagnosis of dual energy tomosynthesis images.

In another embodiment, as shown in FIG. 19, a dual energy CAD system 900 uses high and low energy tomosynthesis images $1a$ . . . 1N 916 and $2a$ . . . 2N 917, respectively, as well as soft tissue images 1 . . . N 219 and bone images 1 . . . N 218 (or alternatively first decomposed images and second decomposed images) as image data 915, such that data source 910 includes image data 915, image acquisition data 212, and patient demographic data 214. Otherwise, the CAD system 900 is similar to system 200 described with respect to FIG. 6. Alternatively, the operations 220, 230, 240 may be performed in parallel on each tomosynthesis image and each soft tissue image and bone image as described with respect to FIG. 7.

While tomosynthesis CAD 800 and DE tomosynthesis CAD 900 are described in FIGS. 18 and 19, it is further contemplated that multiple energy tomosynthesis CAD may be employed using the methods described with respect to FIG. 12, that is, the method shown in FIG. 19 may be expanded to incorporate additional energies.

It should be noted that all of the methods described above may be employed within the imaging system 100, and in particular, may be stored within memory 112 and processed by processing circuit 110. It is further within the scope of this invention that the disclosed methods may be embodied in the form of any computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or as data signal transmitted whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for computer aided processing of dual or multiple energy images within a processing circuit, the method comprising:
    employing a data source, the data source including a dual or multiple energy image set, the image set comprising four distinct images comprising a high energy image, a low energy image, a bone image, and a soft tissue image;
    defining a region of interest within an image from the dual or multiple energy image set;
    extracting a set of features from the region of interest based on image attributes from all of the four distinct images of the image set, the features comprising computed features, measured features, or both; and
    overlaying the extracted features on the region of interest.

2. The method of claim 1, further comprising employing a feature selection algorithm on the region of interest and classifying the region of interest.

3. The method of claim 2, further comprising incorporating prior knowledge from training for classifying the region of interest.

4. The method of claim 3, wherein incorporating prior knowledge from training includes computing features on known samples of different normal and pathological medical conditions.

5. The method of claim 4, wherein the feature selection algorithm sorts through the features of known samples, selects useful features of known samples, and discards features of known samples which do not provide useful information.

6. The method of claim 2, wherein classifying the region of interest using an optimal set of features comprises classifying one or more medical conditions.

7. The method of claim 1, wherein processing dual or multiple energy images comprises detecting and diagnosing one or more medical conditions.

8. The method of claim 1, wherein defining a region of interest comprises manually selecting a region of interest.

9. The method of claim 1, wherein defining a region of interest comprises utilizing an automated algorithm with or without user specifications input.

10. The method of claim 1, wherein the data source further includes at least one of image acquisition system information and demographic information, symptoms, and history of patient, wherein the image acquisition system information, demographic information, symptoms, and history of patient serve as feature measures in the feature extraction.

11. The method of claim 1, wherein the data source includes dual or multi-energy volumetric CT data wherein the feature extraction is performed based on volumetric image attributes.

12. The method of claim 1, wherein the data source includes dual or multi-energy X-ray tomosynthesis multi-energy data wherein the feature extraction is performed based on volumetric image attributes.

13. The method of claim 1, further comprising indicating at least one classified region using a marker on a display of each image within the dual or multiple energy image set where the at least one classified region is located.

14. The method of claim 13, further comprising displaying a single image which incorporates all markers from each image within the dual or multiple energy image set.

15. A system for computer aided processing of dual energy images, the system comprising:
    a detector generating a first image representative of photons at a first energy level passing through a structure and a second image representative of photons at a second energy level passing through the structure;
    a memory coupled to the detector, the memory storing the first image and the second image;
    a processing circuit coupled to the memory, the processing circuit processing a dual energy image set including a bone image, a soft tissue image, a high energy image, and a low energy image;
    storing the dual energy image set in the memory as a data source;
    defining a region of interest within an image from the dual energy image set;
    extracting a set of features from the region of interest based on image attributes from all of the four images of the image set, the features comprising computed features, measured features, or both; and
    a displaying device coupled to the processing circuit, the displaying device displaying at least one feature.

16. A storage medium encoded with a machine readable computer program code, said code including instructions for causing a computer to implement a method for aiding in processing of dual or multiple energy images, the method comprising:
    employing a data source, the data source including a dual or multiple energy image set the image set comprising four distinct images comprising a high energy image, a low energy image, a bone image, and a soft tissue image;
    defining a region of interest within an image from the dual or multiple energy image set;
    extracting a set of features from the region of interest based on image attributes from all of the four images of the image set, the features comprising computed features, measured features, or both; and
    overlaying the extracted features on the region of interest.

17. The method of claim 16, further comprising employing a feature selection algorithm on the region of interest and classifying the region of interest.

18. The method of claim 17, further comprising incorporating prior knowledge from training for classifying the region of interest.

19. The method of claim 18, wherein incorporating prior knowledge from training includes computing features on known samples of different normal and pathological medical conditions.

20. The method of claim 19, wherein the feature selection algorithm sorts through the features of known samples, selects useful features of known samples, and discards features of known samples which do not provide useful information.

* * * * *